US00PP29787P3

(12) United States Plant Patent
Finn

(10) Patent No.: US PP29,787 P3
(45) Date of Patent: Nov. 6, 2018

(54) BLUEBERRY PLANT NAMED 'ECHO'

(50) Latin Name: ***Vaccinium* spp. section *Cyanococcus* L.**
Varietal Denomination: Echo

(71) Applicant: The United States of America, as Represented by the Secretary of Agriculture, Washington, DC (US)

(72) Inventor: Chad E. Finn, Corvallis, OR (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/530,947

(22) Filed: Mar. 28, 2017

(65) Prior Publication Data

US 2018/0288913 P1 Oct. 4, 2018

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — John Fado; Ariel Atkinson

(57) ABSTRACT

'Echo' is a new and distinct repeat flowering, ornamental blueberry (*Vaccinium* section *Cyanococcus* L.) cultivar that originated from seed produced from the cross of the female blueberry plant 'Perpetua' (U.S. Plant Pat. No. 24,209) and the male blueberry plant ORUS 55-1 (unpatented). 'Echo' is a blueberry clone distinguished by its ornamental characteristics that include a spreading bush habit with glossy leaves, repeat flowering and fruiting, and small, mild flavored dark blue fruit.

3 Drawing Sheets

Figure 1:
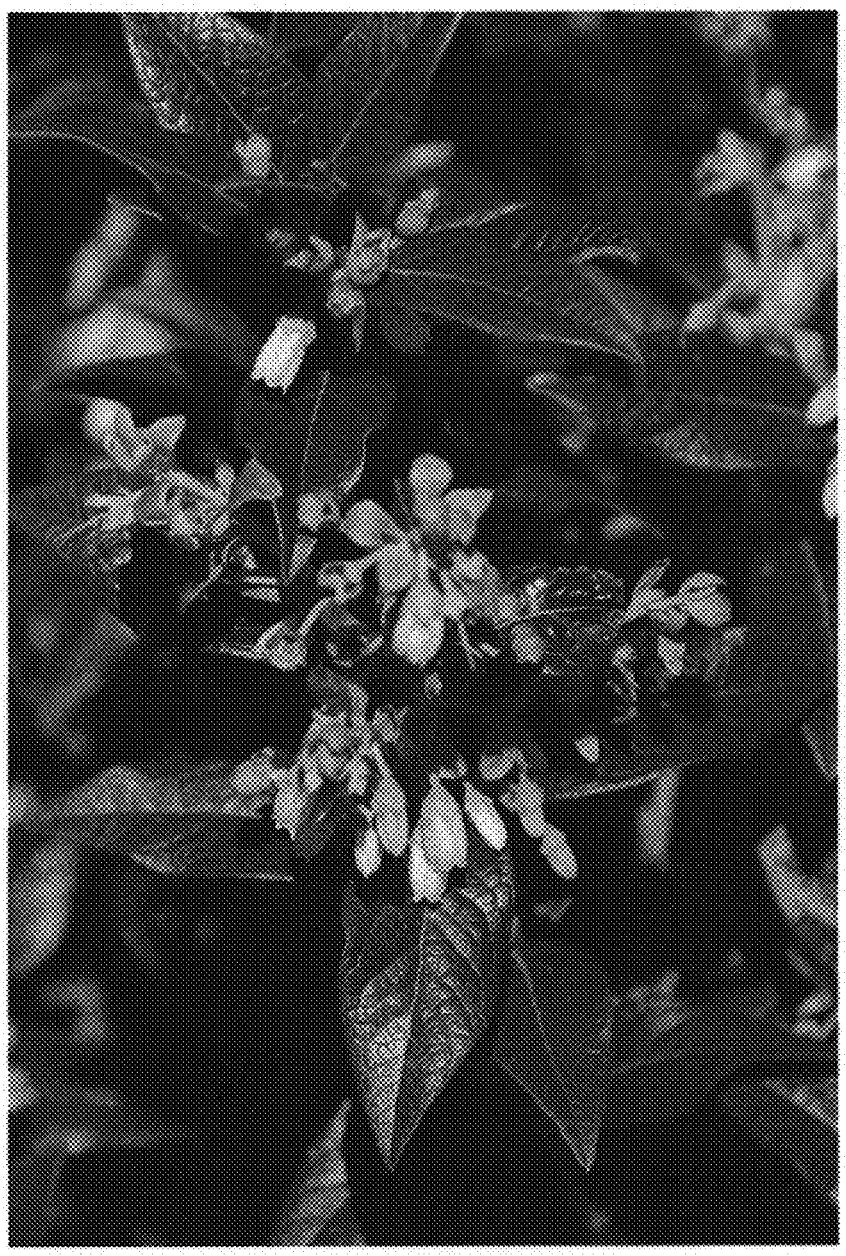

Latin name of genus and species of the plant claimed: 'ECHO' is a new blueberry plant that is a genus *Vaccinium* spp. section *Cyanococcus* L.

Variety denomination: The new blueberry plant claimed is of the cultivar denomination 'Echo'.

BACKGROUND OF THE INVENTION

The present invention relates to a new and distinct blueberry cultivar botanically known as *Vaccinium* section *Cyanococcus* L., and herein referred to as 'Echo', as herein described and illustrated.

'Echo' is a blueberry clone distinguished by its ornamental characteristics that include a spreading bush with glossy leaves, repeat flowering and fruiting, and small, mild flavored dark blue fruit. This new blueberry cultivar was developed in Corvallis, Oreg. in July 2010 and originated from the cross of the female blueberry plant 'Perpetua' (U.S. Plant Pat. No. 24,209) and the male blueberry plant ORUS 55-1 (unpatented) made in Corvallis, Oreg. in 2006. Both parents are repeat flowering and their ancestry can be traced in part to selections CVAC 45 (PI 296412), which was collected from the wild in 1963 in Monmouth, Me. and CVAC (296397), which was collected from the wild in 1964 in Farmington, Me., and are listed as *Vaccinium corymbosum* L. (highbush blueberry) by the USDA—ARS, National Genetic Resources Program, Germplasm Resources Information Network—(GRIN) (Online Database). Since the wild germplasm ancestry originated from where the ranges of *V. corymbosum* and *V. angustifolium* Aiton (lowbush blueberry) overlap and since many of the plant's characteristics for fruit size, leaf shape, and leaf size are intermediate between these two species, 'Echo' is presumed to contain both species in its pedigree. 'Echo's overwintering buds break in the spring, flower and produce a crop like most blueberry plants. 'Echo', as with its 'Perpetua' (U.S. Plant Pat. No. 24,209) maternal parent, is unique in that the new growth produces flower buds that proceed to break bud without winter dormancy and then flower and ripen a late-summer into fall crop. While it is not uncommon for blueberry genotypes to produce a few fruit in the fall on 1-2 buds at the tip of the new growth, these repeat flowering genotypes will flower on up to 12-16 nodes on the new growth. The original seedling of the new cultivar was asexually propagated at a nursery in Benton County, Oreg. The new cultivar was established in vitro from a stem cutting and microcuttings have been taken and rooted from this sort of culture. The present invention has been found to be stable and reproduce true to type through successive asexual propagations.

SUMMARY OF THE INVENTION

The following are the most outstanding and distinguishing characteristics of this new cultivar when grown under normal horticultural practices in Oregon. 1. Ability to flower multiple times in the season on overwintered canes and on new growth; 2. Attractive combination of flowers and fruit in late summer and fall; 3. Green, glossy, attractive leaves; 4. Edible dark blue fruit; and 5. Vigorous, spreading plant habit.

BRIEF DESCRIPTION OF THE PHOTOGRAPHS

Figure 2:
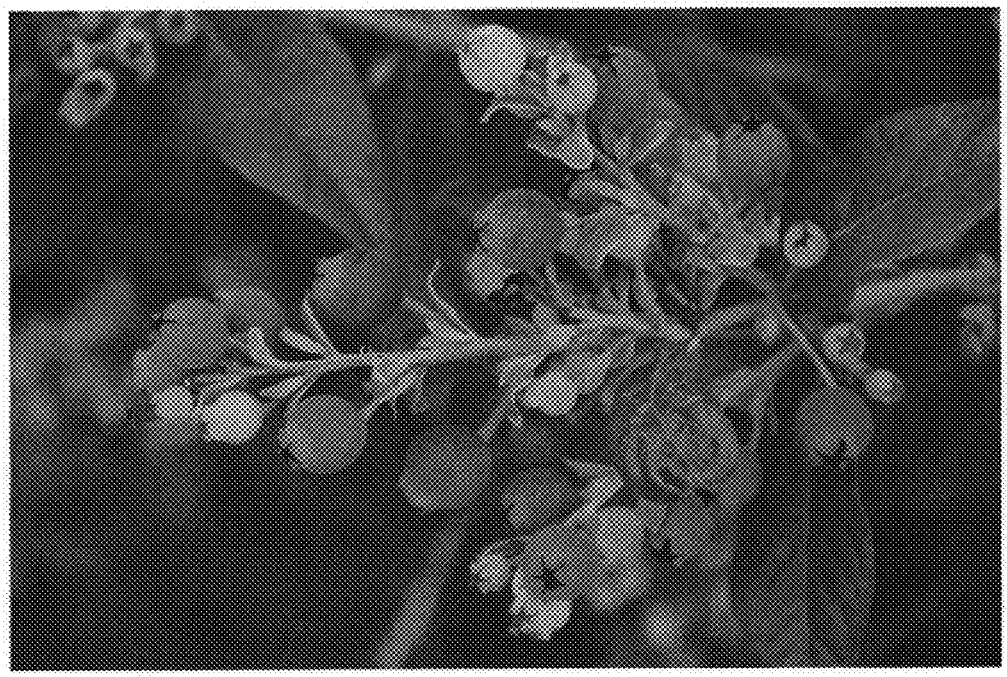
Figure 3:
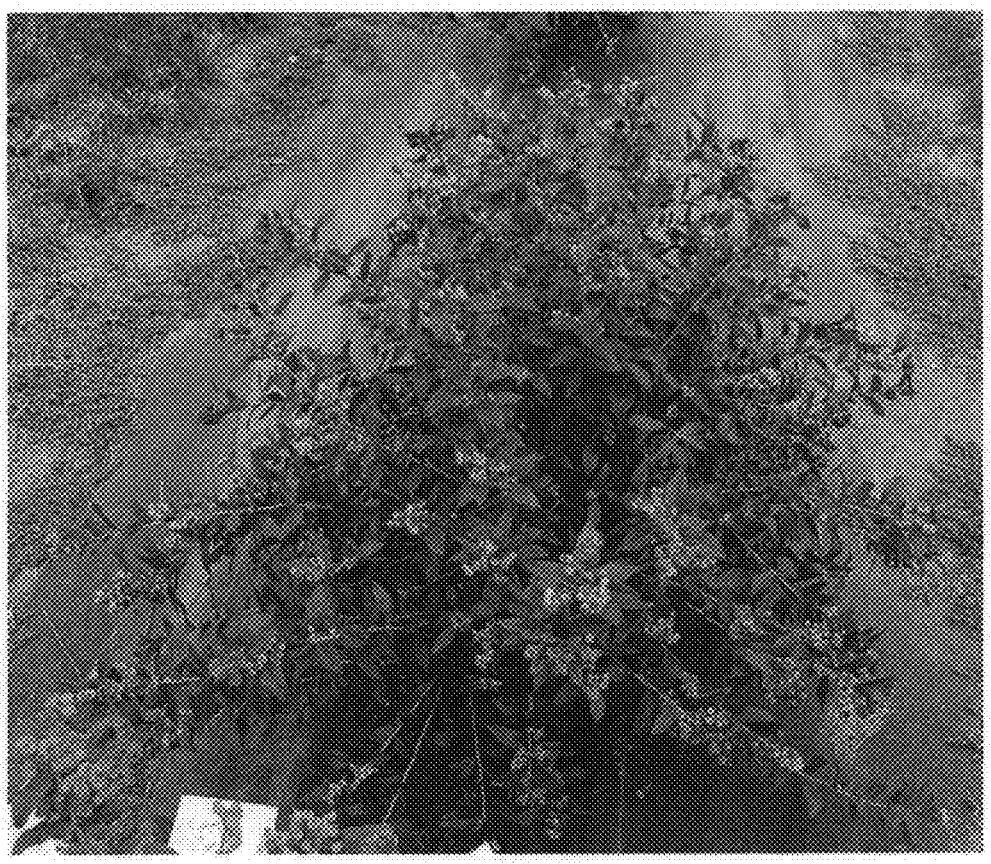

This new blueberry plant is illustrated by the accompanying color photographs that show typical specimens of the flower clusters in bloom (FIG. 1), ripe fruit on a four-year-old plant (FIG. 2), and the entire plant with a ripening crop in late August ($2^{nd}$ crop) (FIG. 3); the colors shown are as true as can be reasonably obtained by conventional photographic procedures.

DETAILED DESCRIPTION OF THE NEW CULTIVAR

The following detailed description of 'Echo' is based on observations taken from 2013 to 2016 in trials planted in 2012 in Corvallis and Aurora, Oreg. The measurements/observations for one trait always being made on samples from the same location. This description is in accordance with UPOV terminology. Color designations, color descriptions and other phenotypical descriptions may deviate from the stated values and descriptions depending upon variation in environmental, seasonal, climatic and cultural conditions. 'Echo' has not been observed under all possible environmental conditions. Color terminology follows The Royal Horticultural Society Colour Chart. London (R.H.S.) ($5^{th}$ edition, 2007).

Table 1 shows most the bush characteristics of the new cultivar. Characteristics include plant size, height of plant, canopy diameter, growth habit, plant vigor, twigginess, suckering, tendency towards evergreenness, surface texture 1 year-old-wood, surface texture 3 year-old-wood, color new wood, color rough bark 1 year-old-wood, color rough bark 3 year-old-wood, internode length and winter hardiness in Aurora, Oreg. (45° 16' 49" N/122° 44' 50" W).

TABLE 1

| Characteristic | Echo |
|---|---|
| Plant size | Small; comparable to 'Perpetua' |
| Height of plant | 0.88 m |
| Canopy diameter | 0.90 m |
| Growth habit | Upright and spreading compared to 'Perpetua' |
| Plant vigor | Moderate vigor, comparable to 'Perpetua' |
| Twigginess | Moderate |
| Suckering | None |
| Tendency towards evergreenness | Deciduous but holds leaves into winter |
| Surface texture new wood | Smooth, slightly pubescent |
| Surface texture 1 year-old-wood | Smooth, slightly pubescent |
| Surface texture 3 year-old-wood | Rough |
| Color new wood | Gray-Red group 180A |
| Color rough bark 1 year-old-wood | Gray-Red group 178B |
| Color rough bark 3 year-old-wood | Greyed-Orange group 177A |
| Internode length | 1.84 cm |
| Winter tolerance in Aurora, Oregon (45° 16' 49" N/122° 44' 50" W) | Excellent |

Table 2 shows the foliage characteristics of the new cultivar. Characteristics include leaf length, leaf width, leaf shape, leaf margin, leaf color upper leaf surface, leaf color lower leaf surface, pubescence upper leaf surface, pubescence lower leaf surface, pubescence leaf margins, and leaf venation.

TABLE 2

| Characteristic | Echo |
|---|---|
| Leaf length | 4.72 cm |
| Leaf width | 1.89 cm |
| Leaf shape | Elliptic |

TABLE 2-continued

| Characteristic | Echo |
|---|---|
| Leaf margin | Entire |
| Leaf color upper leaf surface | Green group 139A |
| Leaf color lower leaf surface | Green group 138B |
| Pubescence upper leaf surface | None visible |
| Pubescence lower leaf surface | None visible |
| Pubescence leaf margins | None visible |
| Leaf venation | Net |
| Shape of leaf apex | Acuminate |
| Shape of leaf base | Acute |
| Petiole length | 1.84 mm |
| Petiole diameter | 1.23 |
| Petiole color | Yellow-Green Group (145B) |

Table 3 shows the flower characteristics of the new cultivar. Characteristics include fragrance, pedicel length flower—spring, peduncle length flower—spring, flower shape, pollen abundance, pollen color, flower length, corolla length, corolla diameter, style length, calyx diameter, corolla aperture, calyx surface, corolla color, corolla texture, calyx color, pistil color, pedicel color, peduncle color, flowering cluster, spring flowering period (mean date ~5%), spring flowering period (mean date ~50%), summer flowering period (mean date ~5%), number flowers per cluster, Fruit set when pollinated with bulk pollen of other cultivars, Fruit set when pollinated with own pollen (selfed), stigma location (distance from corolla aperture to stigma), pollen abundance, pollen color, calyx aperture, calyx lobes, calyx depth and flower arrangement.

TABLE 3

| Characteristic | Echo |
|---|---|
| Fragrance | None |
| Pedicel length flower - spring | 4.90 mm |
| Peduncle length flower - spring | 7.66 mm |
| Flower shape | Urceolate |
| Pollen abundance | High |
| Pollen color | Yellow group 10D |
| Flower length | 8.8 mm |
| Corolla length | 7.6 mm |
| Corolla diameter | 5.0 mm |
| Style length | 7.1 mm |
| Calyx diameter | 4.5 mm |
| Corolla aperture | 3.4 mm |
| Calyx surface | Smooth |
| Corolla color | White group 155A |
| Corolla texture | Smooth |
| Calyx color | Yellow-Green group 146B |
| Pistil color | Yellow-Green group 145A |
| Pedicel color | Yellow-Green group 146C |
| Peduncle color | Yellow-Green group 145A |
| Flowering cluster | Loose |
| Spring flowering period (mean date ~5%) | Mar. 18 |
| Spring flowering period (mean date ~50%) | Apr. 1 |
| Summer flowering period (mean date ~5%) | Jul. 7 |
| Number flowers per cluster | 7.3 |
| Fruit set when pollinated with bulk pollen of other cultivars | 95.4% |
| Fruit set when pollinated with own pollen | 55.2% |
| Stigma location | Below corolla aperture, inside corolla |
| Pollen abundance | High |
| Pollen color | Yellow group 10D |
| Calyx aperture | 2.48 mm |
| Calyx lobes | 2.26 mm |
| Calyx depth | 1.75 mm |
| Flower arrangement | Monopodial branching |

Table 4 shows the mature fruit characteristics of the new cultivar. Characteristics include berry cluster, berry peduncle length, berry pedicel length, berry detachment from pedicel, berry weight, berry height, berry width, berry height/width ratio, berry shape, berry skin color on plant, berry skin color after harvest, berry skin color after polishing, berry wax, berry flesh color, pedicel scar, berry firmness, berry flavor, berry texture, color of dried seeds, length of well-developed dried seed, width of well-developed dried seed, weight of well-developed dried seed, productivity and size of $1^{st}$ (spring) vs $2^{nd}$ (summer) crop.

TABLE 4

| Characteristic | Echo |
|---|---|
| Berry cluster | Loose |
| Berry peduncle length | 26.73 mm |
| Berry pedicel length | 5.71 mm |
| Berry detachment from pedicel | Slight resistance to pull |
| Berry weight | 0.75 g |
| Berry height | 12.21 mm |
| Berry width | 11.94 mm |
| Berry height/width ratio | 1.12 |
| Berry shape | Subglobose |
| First ripe (5%) fruit first (spring) crop | May 24 |
| First ripe (5%) fruit first (spring) crop | Aug. 19 |
| Berry skin color on plant when ripe | Violet-Blue group N92C |
| Berry skin color after harvest | Violet-Blue group N92C |
| Berry skin color after polishing harvested fruit | Blue group 103A |
| Berry wax | Present |
| Berry flesh color | Green group 139D |
| Pedicel scar | 1.59 mm |
| Berry firmness | Moderately firm |
| Berry flavor | Mild |
| Berry texture | Firm, do not notice seeds |
| Color of dried seeds | Greyed-Orange group 177C |
| Length of well-developed dried seed | 1.76 mm |
| Width of well-developed dried seed | 0.84 mm |
| Weigh of well-developed dried seed | 0.40 mg |
| Productivity | Moderate; comparable to 'Perpetua' |

TABLE 4-continued

| Characteristic | Echo |
|---|---|
| Size of 1st (spring) vs 2nd (summer) crop | 2nd crop is larger than first |

Resistance to diseases and insects: In a minimal spray program with dormant sprays only, 'Echo' has had no fungal or bacterial disease symptoms and no indication of problems with gall midge. 'Echo' plants have not yet shown symptoms or tested positive for Blueberry shock virus; if it was an extremely susceptible (e.g. 'Bluegold' (unpatented)), it would be showing symptoms and testing positive after 5 years in the field, however, it is too soon to characterize it as slow to get the virus.

COMPARISON WITH PARENTAL AND COMMERCIAL CULTIVARS

'Echo' differs from the female parent 'Perpetua' (U.S. Plant Pat. No. 24,209), which is also the closest comparable commercial cultivar, in that its fruit appear longer as they have a greater length to width ratio, the fruit are a much darker violet-blue and the plants are broader and more spreading than upright with grey-red vs olive-green bark and the leaves are narrower and smaller.

'Echo differs from the male parent ORUS 55-1 (unpatented) in that the fruit are much more blue than black and the plant is more compact with glossy leaves.

I claim:

1. A new and distinct cultivar of blueberry plant, substantially as illustrated and described, characterized by its ability to flower on new growth without any chilling; attractive combination of flowers and fruit in late summer and fall; dark green, glossy, attractive leaves; edible, dark blue fruit; and vigorous and compact, spreading, plant habit.

* * * * *